(12) United States Patent
Ahmed et al.

(10) Patent No.: US 6,974,466 B2
(45) Date of Patent: Dec. 13, 2005

(54) LIGATING BAND DELIVERY APPARATUS

(75) Inventors: Munir Ahmed, Columbus, OH (US); Victor D. Clark, Jr., Pfafftown, NC (US); Scott Reed, Advance, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 0 days.

(21) Appl. No.: 10/012,871

(22) Filed: Dec. 5, 2001

(65) Prior Publication Data

US 2002/0072757 A1 Jun. 13, 2002

Related U.S. Application Data

(60) Provisional application No. 60/251,553, filed on Dec. 6, 2000.

(51) Int. Cl.$^7$ .............................................. A61B 17/12
(52) U.S. Cl. ..................................... 606/140; 606/139
(58) Field of Search ............................... 606/140, 139, 606/141, 170

(56) References Cited

U.S. PATENT DOCUMENTS

| | | | |
|---|---|---|---|
| 3,760,810 A | * | 9/1973 | Van Hoorn .................. 606/140 |
| 4,257,419 A | * | 3/1981 | Goltner et al. .............. 606/140 |
| 4,621,635 A | | 11/1986 | Ali |
| 4,940,468 A | * | 7/1990 | Petillo ......................... 606/170 |
| 5,158,563 A | | 10/1992 | Cosman |
| 5,224,497 A | | 7/1993 | Ehlers |
| 5,269,789 A | | 12/1993 | Chin et al. |
| 5,318,578 A | | 6/1994 | Hasson |
| 5,320,630 A | | 6/1994 | Ahmed |
| 5,356,416 A | | 10/1994 | Chu et al. |
| 5,398,844 A | | 3/1995 | Zaslavsky et al. |
| 5,423,834 A | | 6/1995 | Ahmed |
| 5,462,559 A | | 10/1995 | Ahmed |
| 5,464,412 A | | 11/1995 | Budding |
| 5,507,797 A | | 4/1996 | Suzuki et al. |
| 5,527,319 A | | 6/1996 | Green et al. |
| 5,569,268 A | | 10/1996 | Hosoda |

(Continued)

FOREIGN PATENT DOCUMENTS

DE 19834263 2/2000

(Continued)

OTHER PUBLICATIONS

Application of a Multiple-Band Ligator in Active Variceal Bleeding; M. Sackmann et al., Endoscopy, Aug. 1, 1996, vol. 28, No 6, p. 533.

(Continued)

*Primary Examiner*—Julian W. Woo
(74) *Attorney, Agent, or Firm*—Brinks Hofer Gilson & Lione

(57) ABSTRACT

A apparatus is disclosed that is adapted for delivery of a multiplicity of pre-loaded ligating bands within patient, such as to treat hemorrhoidal tissue. The apparatus comprises a delivery member that includes a tissue receiving chamber at the distal end that communicates with a passageway that represents part of the main suction pathway that connects with a suction means. The proximal portion of the apparatus includes an actuating mechanism that is operatively connected to one or more band carrier elements, such as strands with bead-like retainers, which receive and urge the ligating bands over the delivery member for deployment. The actuating mechanism and suction actuating interface are configured such that they can be controlled while the operator retains the other hand for another operation, such as to manipulate an anoscope. In one embodiment, the proximal portion includes a pistol-shaped grip portion, while the actuating mechanism comprises a knurled wheel.

18 Claims, 12 Drawing Sheets

U.S. PATENT DOCUMENTS

| | | |
|---|---|---|
| 5,624,453 A | 4/1997 | Ahmed |
| 5,651,788 A | 7/1997 | Fleischer et al. |
| 5,681,328 A | 10/1997 | Lamport et al. |
| 5,697,940 A | 12/1997 | Chu et al. |
| 5,741,273 A | 4/1998 | O'Regan |
| 5,788,715 A | 8/1998 | Watson, Jr. et al. |
| 5,853,416 A | 12/1998 | Tolkoff |
| 5,857,585 A | 1/1999 | Tolkoff et al. |
| 5,913,865 A | 6/1999 | Fortier et al. |
| 5,968,056 A | 10/1999 | Chu et al. |
| 5,972,009 A | 10/1999 | Fortier et al. |
| 5,976,158 A | 11/1999 | Adams et al. |
| 5,980,537 A | 11/1999 | Ouchi |
| RE36,629 E | 3/2000 | Zaslavsky et al. |
| 6,042,591 A | 3/2000 | Mears |
| 6,051,003 A | 4/2000 | Chu et al. |
| 6,059,719 A | 5/2000 | Yamamoto |
| 6,059,797 A | 5/2000 | Mears |
| 6,059,798 A | 5/2000 | Tolkoff |
| 6,066,147 A | 5/2000 | Mears |
| 6,136,009 A | 10/2000 | Mears |
| 6,149,659 A | 11/2000 | Ahmed |
| 6,235,040 B1 | 5/2001 | Chu et al. |
| 6,547,798 B1 * | 4/2003 | Yoon et al. ............ 606/141 |

FOREIGN PATENT DOCUMENTS

| | | | |
|---|---|---|---|
| WO | 9408517 | 4/1994 | |
| WO | 9512355 | 5/1995 | |
| WO | 9624292 | 8/1996 | |
| WO | 9732528 | 9/1997 | |
| WO | 9746161 | 12/1997 | |
| WO | 9953847 | 10/1999 | |
| WO | 9956635 | 11/1999 | |
| WO | 9965402 | 12/1999 | |
| WO | WO 99/65400 | * 12/1999 | ......... A61B 17/12 |

OTHER PUBLICATIONS

New Rubber-Band Loader to Facilitate Use of Hemorrhoid Ligator; Mitsuyo Kosugi et al.; Diseases of the Colon and Rectum; Oct. 1, 1998, vol. 41, No 10, p. 1328.

The First Reusable Multi-Band Ligator for Endoscopic Hemostasis of Variceal Bleeding, Nonvariceal Bleeding and Mucosal Resection; C. Ell et al; Endoscopy, Nov. 1, 1999; 31(0); pp. 738-740.

* cited by examiner

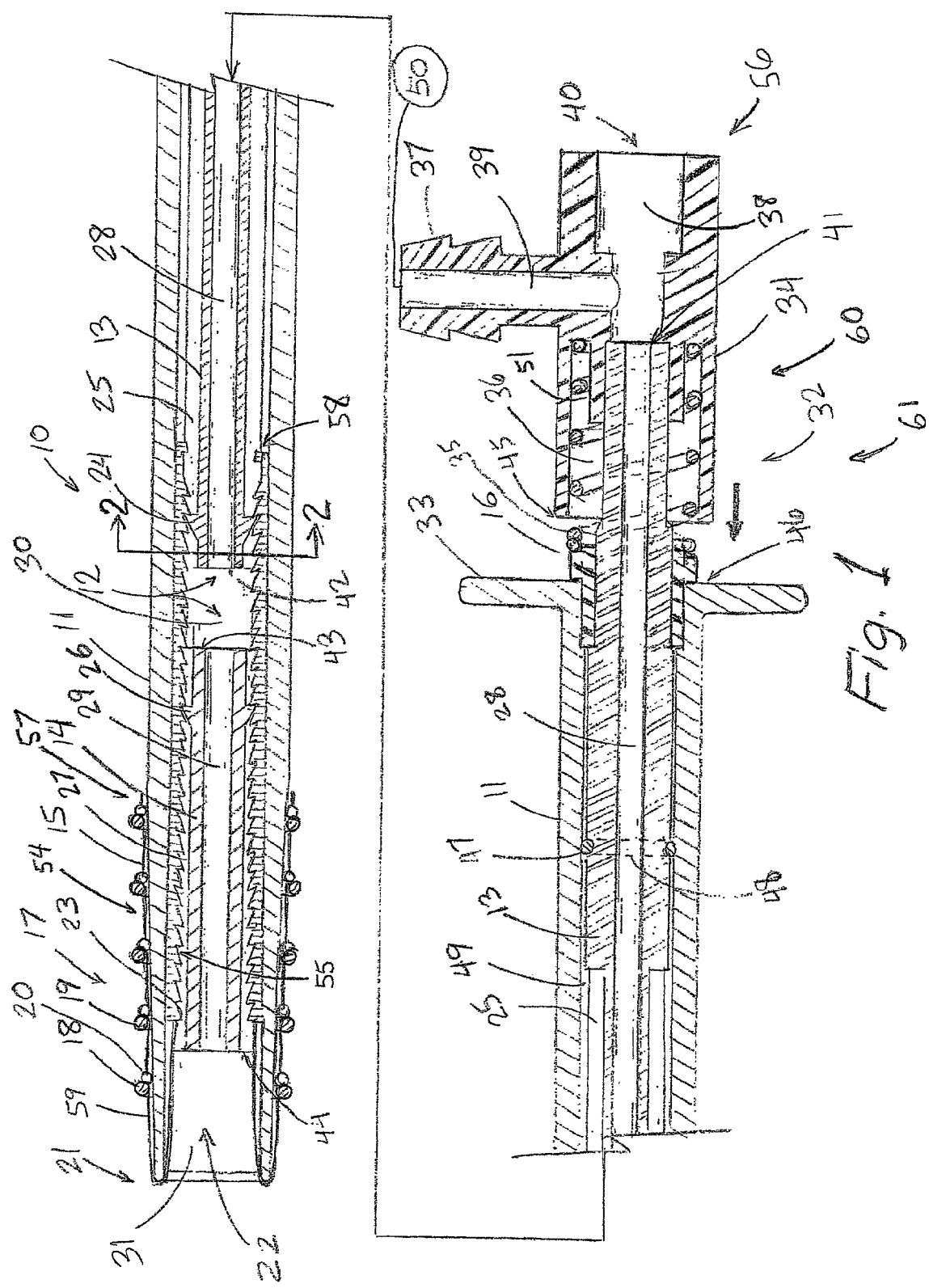

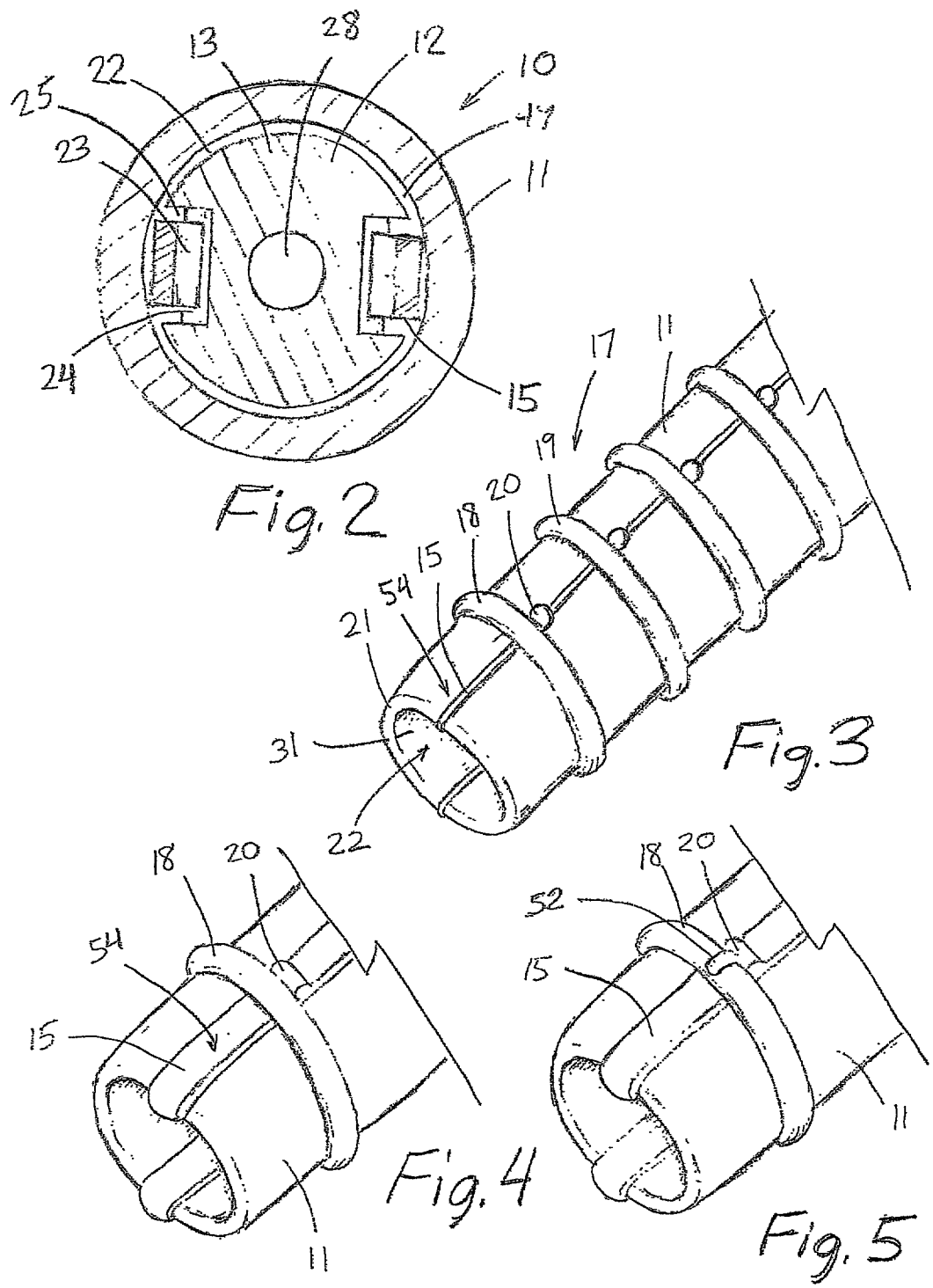

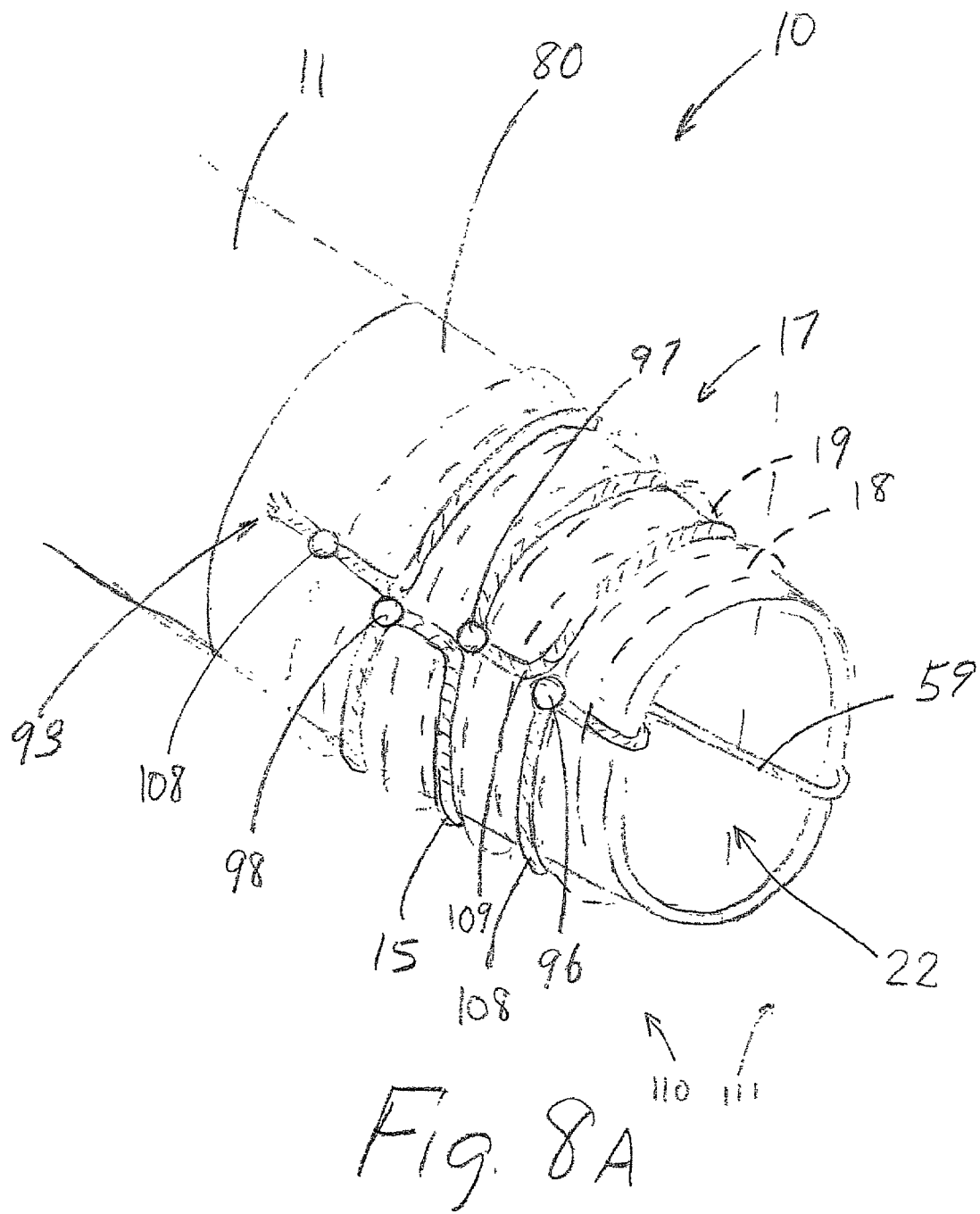

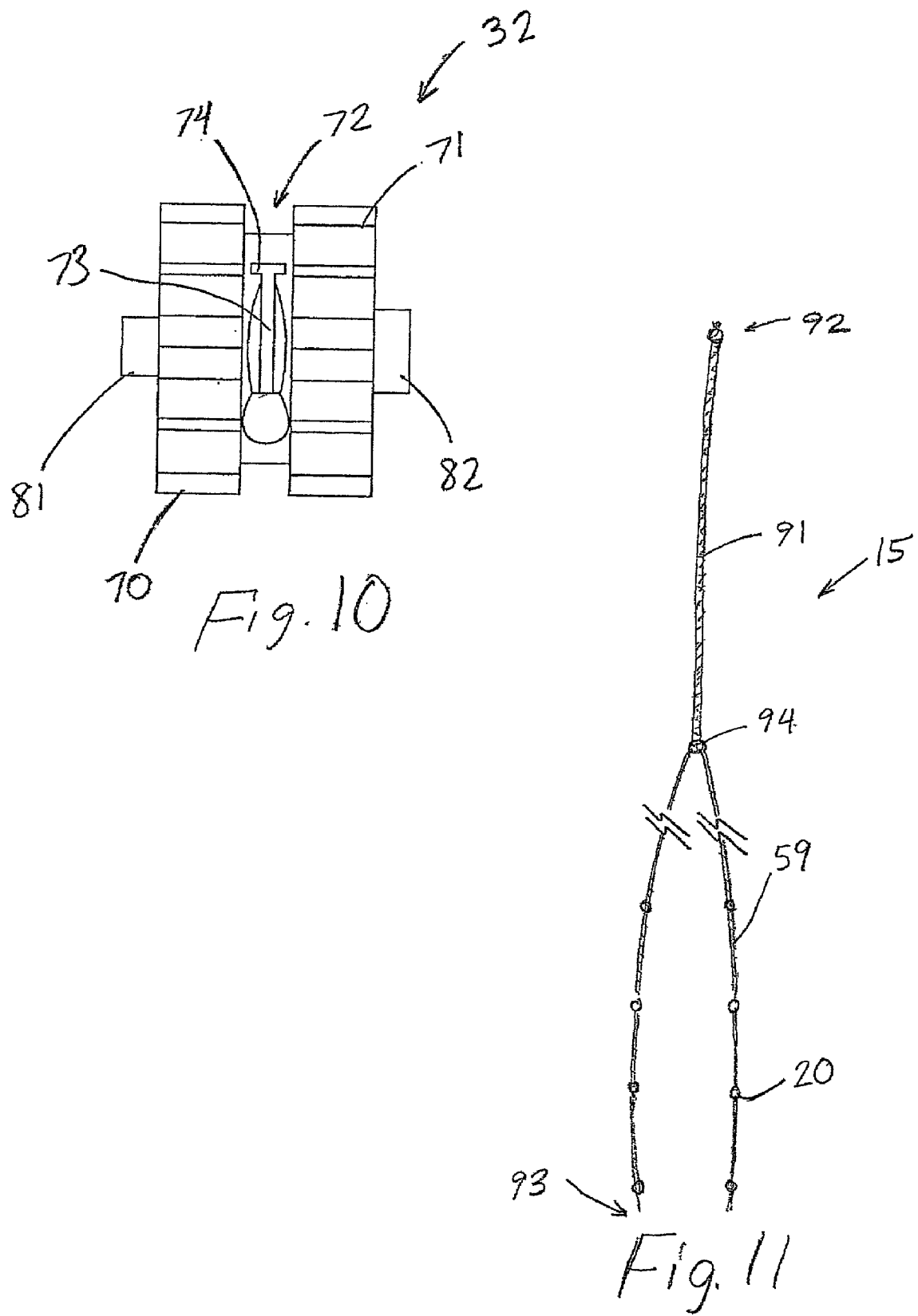

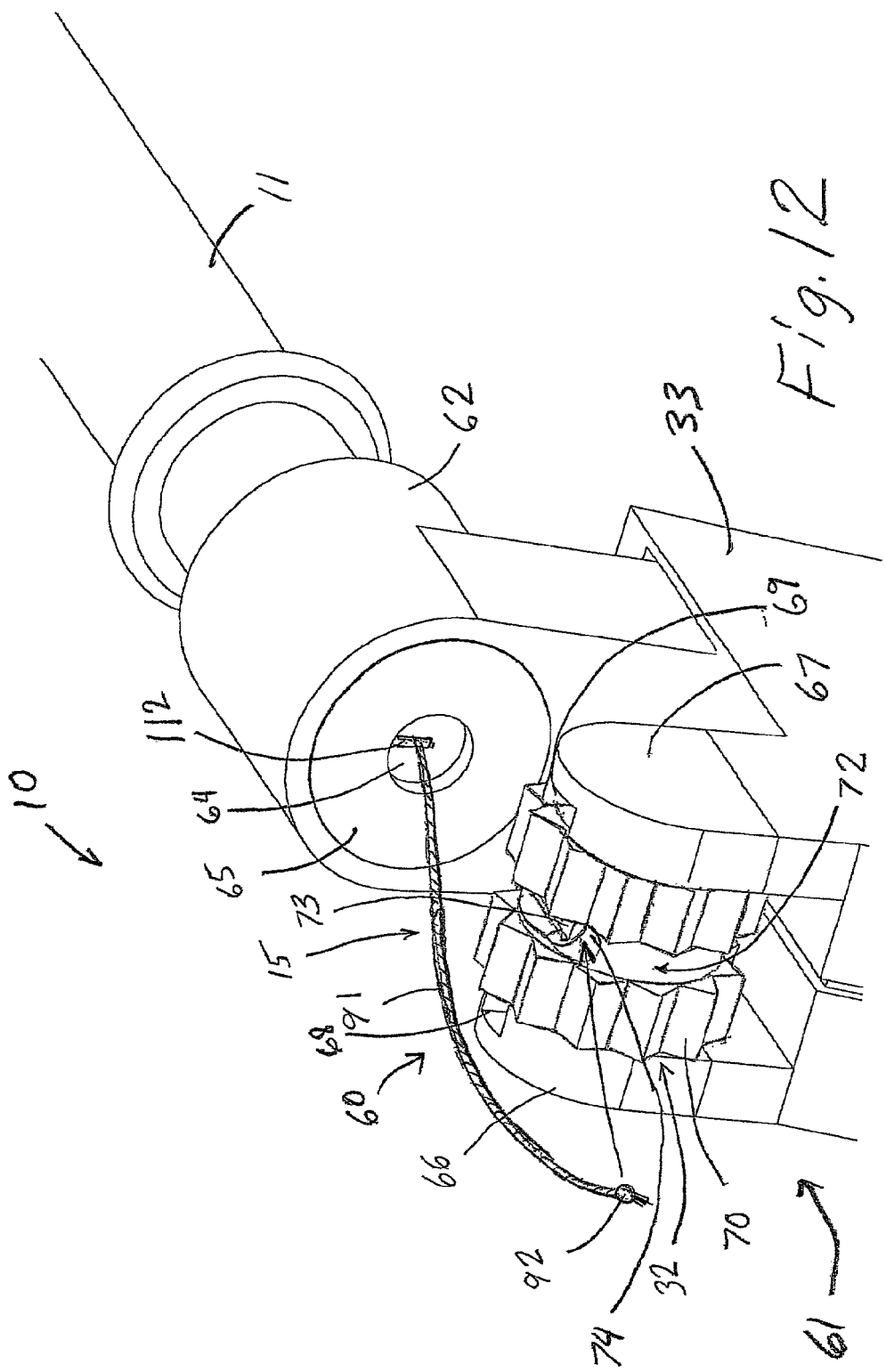

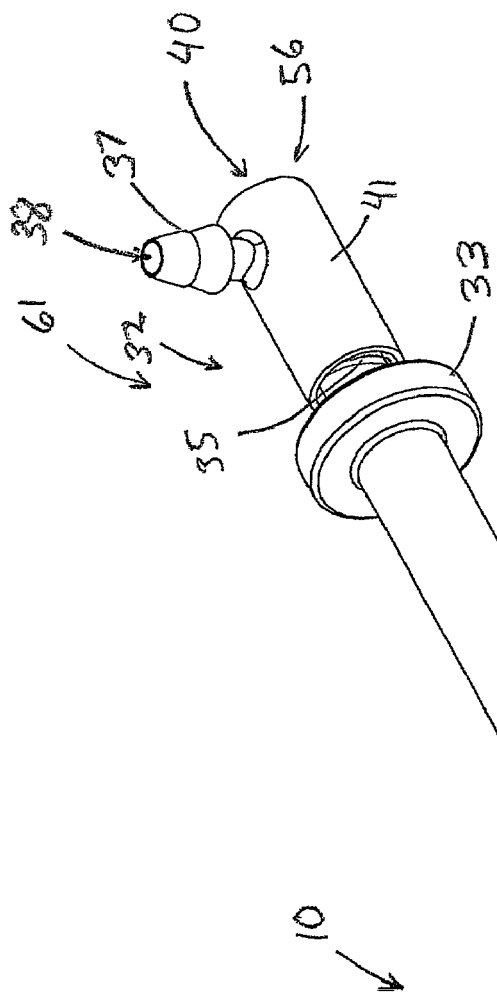
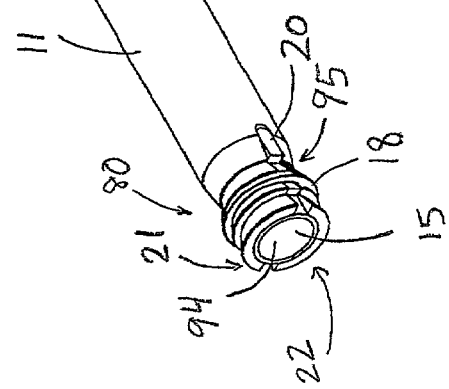
FIG. 13

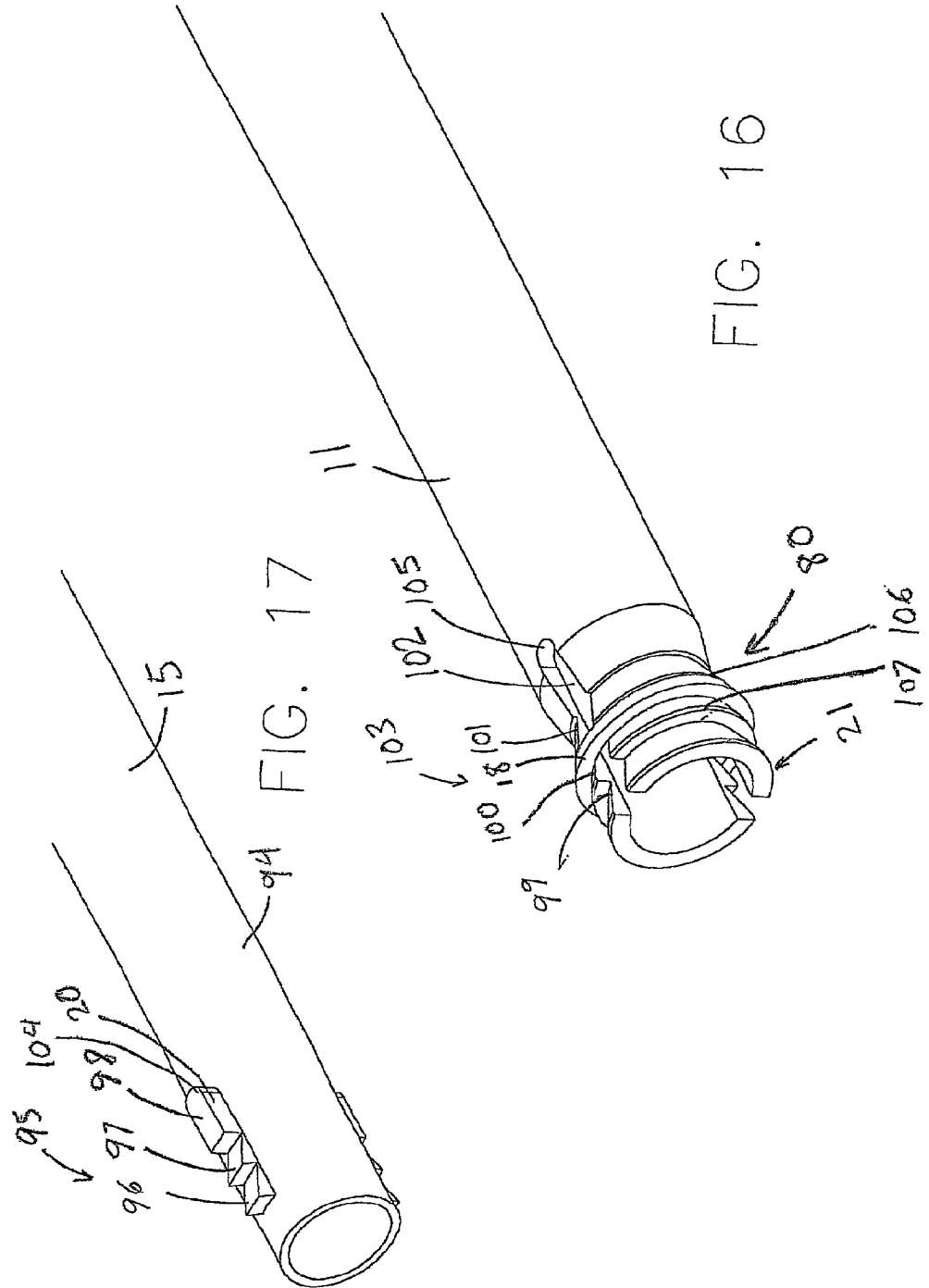

LIGATING BAND DELIVERY APPARATUS

RELATED APPLICATION

This application claims priority of provisional application Ser. No. 60/251,553, filed Dec. 6, 2000.

TECHNICAL FIELD

This device is related to medical devices and more particularly, to instruments for deploying a ligating band.

BACKGROUND OF THE INVENTION

Ligation involves applying a band or ligature around a portion of tissue, thereby cutting off blood or fluid flow and causing the tissue to necrose and separate from adjacent healthy tissue. It is widely used to treat a number of medical conditions, including, but not limited to, hemorrhoids, polyps, ballooning varices, and other types of lesions, including those that are cancerous. Various types of instrumentation have been developed that are capable of deploying one or more preloaded ligating bands with the emphasis being on minimally-invasive devices that can be introduced through a natural body opening. The two primary types of ligating band dispensers are those designed to fit over, or work within an endoscope for treating sites that cannot be viewed directly, and simpler, stand-alone devices designed for situations where use of a standard endoscope is not necessary or required. Typically, both types are used with a suction or vacuum means to draw the tissue into the distal tip, whereby the band is deployed over the base of the diseased tissue to cut off blood flow.

In certain instances, it may become necessary or desirable to deploy more than a single ligating band during a procedure. To prevent having to withdraw the instrument from the patient, reload, and reintroduce it for treating additional lesions, devices have been developed capable of sequentially delivering multiple bands that are preloaded, thus shortening the procedure time and improving patient comfort. Typically, multiple band ligating devices include designs with increased mechanical complexity over devices that dispense a single band. One solution to dispensing multiple bands includes individually tethering or otherwise securing the bands to the dispenser and then releasing them sequentially as needed, often by use of one or more strings or wires extending to the proximal end. Various other methods have included using cooperating inner and outer members that slide the individual bands by pushing or pulling them from the tip of the inner or outer member, the bands being preloaded onto the inner or outer member prior to deployment. Unfortunately, each of these methods has been primarily designed for operation with an endoscope and thus, are not ideally suited for incorporation into a separate hand-operated device, which is a highly desirable feature for stand-alone dispensers, such as those used to band hemorrhoids.

Hand-operated ligation band devices are typically less costly to use than types that are used with an endoscope and are especially well-suited when direct access is less of a problem, such as when ligating hemorrhoids. Although a proctoscope or sigmoidoscope may be used for hemorrhoid ligation, these procedures may be conducted 'blind' or 'semi-blind' using the dentate line inside the rectum as a guide for correct positioning of the device. With most hemorrhoids occurring in this vicinity, some physicians do not feel the need to perform the procedure with visual assistance, while others prefer to increase accuracy of placement by using a simple anoscope (a simple funnel-like device) to help position the ligating band dispenser. Thus, it is especially desirable to make these devices operable with a single hand so that the physician can use the other hand to manipulate the anoscope. There is some disagreement with these single band, single-handed ligating band dispensers to the number of bands that can be safely applied per session with most reporting that either two or three should be the maximum attempted. This is due in part to the need for reintroducing the device following each reloading procedure.

An ideal multiple-band dispenser for hemorrhoid ligation should include a suction means to draw the tissue into the tip, it should be operable using a single hand, and it should be capable of delivering the bands precisely and accurately from the tip of the device using a minimal amount of manipulation of the proximal actuating mechanism. A secondary goal is for delivery to be accomplished in a smooth manner, such that there is minimal or no movement of the distal portion of the apparatus during deployment.

SUMMARY OF THE INVENTION

The foregoing problems are solved and a technical advance is achieved in an illustrative multiple ligating band delivery apparatus adapted for single hand operation to treat a hemorrhoid or other readily accessible lesion under direct observation, including using a anoscope. The present invention comprises a delivery member, typically an elongate, tubular member, that is configured for insertion into a body orifice, such as the rectum. The distal portion of the delivery member includes a tissue receiving chamber that is sized to accept a critical amount of tissue, such as a hemorrhoid, over which a ligating band is applied to cause necrosis and eventual elimination of that tissue. The delivery member includes a passageway extending from the tissue receiving chamber to a suction means attachment port. When connected to a suction-creating device, tissue can be drawn into the receiving chamber where a ligating band is deployed over the distal edge of the delivery member (it should be noted that the term 'distal end' is synonymous with 'distal edge' in this application). The delivery member is configured such that a plurality of ligating bands can be placed thereover and then urged distally by one or more band carrier elements that are slidable relative to the delivery member. The band carrier elements, which can comprise either inner or outer members, such as strings, bands, teeth, slidable tubes, etc., are configured to carry or force the ligating bands over the distal edge of the delivery member in a sequential manner when the operator sequentially deploys the actuating mechanism. The actuating mechanism, which that part of an actuating assembly directly manipulated by the operator, is located about the proximal portion of the apparatus, which is that portion of the apparatus that typically remains external to the patient. The actuating assembly can include a variety of configurations, including those in which the proximal actuating mechanism is depressed, advanced, retracted, rotated, or otherwise moved by a portion of the operator's hand, while the suction is selectively sealed off via a suction actuating interface, which preferably comprises an external opening to the main suction passageway which extends from the tissue receiving chamber of the delivery member to the suction means attachment port at located about the proximal portion of the apparatus, which is attachable to a suction-generating means. When the suction actuating port is closed, such as by covering it with a thumb or finger, or by a remote means, such as a foot pedal that operates a valve, it creates suction within the tissue receiving chamber which draws the tissue inward for banding. It is within the concept of this invention that the suction actuating interface be part of, operatively connected to the suction creating means such that the latter can be selectively activated and deactivated without the operator having to use the hand not used to manipulate the ligating band delivery apparatus (e.g., by using a foot pedal or some other means).

In a first illustrative embodiment of the present invention, the ligating band delivery apparatus comprises a tubular delivery member and an actuating mechanism comprising an inner member assembly which includes a slidable engagement member. A plurality of standard ligating bands are preloaded over a pair of band-like band carrier elements, the first portion of each being slidably disposed over the outer surface of the delivery member. The first portion of the band carrier elements includes a plurality of retainers for holding the ligating bands at a selected position thereabout. The retainers are appropriately spaced to allow sequential delivery of the bands as the band carrier elements are advanced toward the distal end of the apparatus. The remaining second portion of each band carrier element is inverted into the passageway of the delivery member and each includes an engagement means, such as tooth-like coupling members that cooperate with the engagement member of the inner member assembly to pull the band carrier elements into the delivery member passageway (this term is broadly defined to encompass any secondary passageways located therein), thereby advancing the ligating bands over the delivery member where they are deployed at the distal tip thereof. The actuating mechanism, which in the illustrative embodiment includes a spring and a handle portion, is advantageously designed such that the band carrier elements are engaged after forward advancement of the actuating mechanism, but not deployed until the advancement mechanism is released. With regard to actuating mechanisms that operate to directly 'push' or urge the band off of the apparatus, the forward-directed force required to do so can be transferred from the actuating mechanism to the tip of the apparatus. This may compromise smooth and accurate delivery of the band in some instances. In the present invention, the forward advancement of the engagement member to engage the band carrier element can be perfomed prior to exact placement of the apparatus at the target site. The apparatus can then be placed over the target tissue that has been drawn into the receiving chamber, and each band is quickly and smoothly dislodged from the distal tip portion as the actuating mechanism is released. The design permits numerous bands be loaded over the delivery member without requiring it to be markedly tapered or stepped down in diameter to facilitate the bands being pushed off the distal tip. This allows for the distal portion of the passageway to receive a maximal amount of tissue if necessary while the delivery member is able to advantageously maintain a minimal outer diameter because the lack of external pusher mechanism.

In the first illustrative embodiment, the engagement member, which comprises a portion of the actuating mechanism, includes a series of intermeshing teeth that are located on the proximal portion of the band carrier elements and the engagement member and the internal engagement assembly that serves to engage and pull the band carrier elements in a proximal direction to release the ligating bands. The internal engagement assembly includes a slidable engagement member that slides over the teeth of the band carrier elements in the forward direction, then engages the teeth as the engagement member travels back toward the proximal position, thereby pulling the band carrier element with it as it is withdrawn. To facilitate this operation in the illustrative embodiment, the actuating assembly comprises an actuating mechanism that includes a handle portion that includes a grip portion, a proximal actuator, and a biasing means such as a compression spring, which is attached to engagement member and permits and controls the bidirectional movement that results the sequential delivery of a series of bands.

The first illustrative embodiment includes a suction means attachment port that communicates with the distal receiving chamber via a series of passageways. The proximal end of the apparatus includes a suction actuating port that also communicates with the suction passageways. The proximal opening is configured such that the operator can cover the opening with a thumb or palm of the hand in which the apparatus is held to create suction at the distal end of the apparatus, or uncover the opening to stop the suction from drawing tissue into the receiving chamber.

In a second illustrative embodiment of the present invention, the proximal portion includes a pistol-type grip portion or handle, while the actuating mechanism comprises a thumb-activated knurled wheel that is rotated to draw back the band carrier element, which comprises a pair of strands connected to a yoke portion connected to the actuating mechanism. The strands carry a series of ligating bands loaded over the distal tip portion of the delivery member. The ligating band carrier elements each include a plurality of retainer elements, such as polymer beads, which urge the ligating bands forward as the strands are drawn into the passageway as the band carrier element is spooled on to the rotating wheel. The knurled wheel is engaged by a rachet mechanism that prevents the wheel from reversing and reducing tension on the band carrier element. The grip portion includes a suction actuating port conveniently located on its distal face or surface such that the operator can selectively open and close the port to control suction at the tissue-receiving chamber, when the apparatus is operatively connected to a suction-creating means, by using a finger of the same hand that holds the apparatus.

In a third illustrative embodiment, the band carrier element of the apparatus comprises an inner tubular member that is slidably disposed within the delivery member. The retainers for urging the ligating bands toward the distal edge of the apparatus, comprise a series of tooth-like projection located on opposing sides of the inner tubular member. The delivery member includes a series of steps at which the bands are loaded prior to deployment. A pair of longitudinal channels permit the projections (retainers) to extend upward through the delivery member to engage the band, as well as allowing the projections to slide distally within the channel to urge the band toward the distal edge of the apparatus. The spring-activated actuating mechanism is similar to that of the first embodiment, with the proximal actuator and biasing member (spring) being operatively connected to the inner tubular member to slide it forward relative to the outer delivery member. The ligating bands are forced to a more distal step with each deployment of the actuating mechanism until they are ultimately pushed over the distal edge.

BRIEF DESCRIPTION OF THE DRAWINGS

FIG. 1 depicts a sectional side view of a ligating band apparatus of the present invention;

FIG. 2 depicts a cross-sectional view of the embodiment of FIG. 1 that is taken along line 2—2;

FIG. 3 depicts a pictorial view of the distal portion of the embodiment of FIG. 1;

FIGS. 4–5 depict pictorial views of additional embodiments of the band carrier elements;

FIG. 8A depicts an enlarged view of the distal tip portion of the embodiment of FIG. 8 and the band carrier element configuration;

FIG. 10 depicts a top view of the knurled wheel (actuating mechanism) of the embodiment of FIG. 8;

FIG. 11 depicts a top view of the band carrier element of the embodiment of FIG. 8;

FIG. 12 depicts a rear pictorial view of the actuating mechanism of the embodiment of FIG. 8;

FIG. 13 depicts another embodiment of the present invention having an inner tubular member with tooth-like retainers to urge the ligating bands toward the distal edge of the apparatus;

FIG. 16 depicts an enlarged perspective view of the distal end of the delivery member of FIG. 13; and FIG. 17 depicts an enlarged perspective view of the distal end of the inner tubular member of FIG. 13.

DETAILED DESCRIPTION

Figure 6:
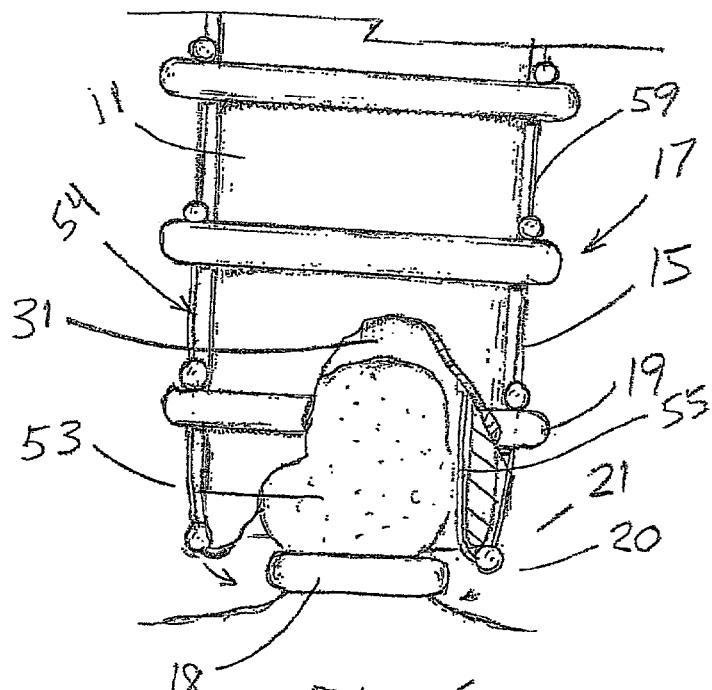
FIG. 6 depicts a partially sectioned view of the distal portion of the embodiment of FIG. 1.

The present invention, depicted in FIGS. 1–17, comprises a ligating band delivery apparatus 10 adapted for hand-held operation to deliver a multiplicity of ligating bands 17 under direct visualization, such as in conjunction with an anoscope for hemorrhoid ligation. The ligating band delivery apparatus 10 includes an delivery member 11, which is typically elongate and tubular in shape for insertion into the patient, one or more band carrier elements 15 that retain a series of ligating bands 7 and sequentially urge them toward the distal edge 21 (distal end) of the delivery member during deployment; a proximal portion 61 that generally remains outside the patient and includes a handle grip 33; a tissue receiving chamber 31 located about the distal end of the delivery member 11 and which communicates with a passageway 22 that extends proximally to connect with an external or integral suction means to draw the tissue into the chamber to be banded; an actuating assembly 60 that includes a proximal actuating mechanism 32 that is operatively connected to the ligating band carrier element(s) 15; and a suction actuating interface 40, such as an opening about the proximal portion, that is configured such that the proximal actuating mechanism 32 and suction actuating interface 40 are controllable by the operator, while the operator's other hand can remain free to manipulate an anoscope or other ancillary device. The term 'sequentially urging' is used to encompass any action performed by the apparatus by which a multiplicity of loaded ligating bands are individually deployable in a controlled manner during a single insertion of the apparatus within a patient. This includes, but is not limited to, having the bands move together as a group toward the distal edge of the apparatus as the actuating mechanism is deployed, or having only the most distal ligating band urged from the distal edge of the apparatus, while the remaining bands are not urged forward until they have assumed the most distal position and are therefore, ready for deployment.

Figure 7:
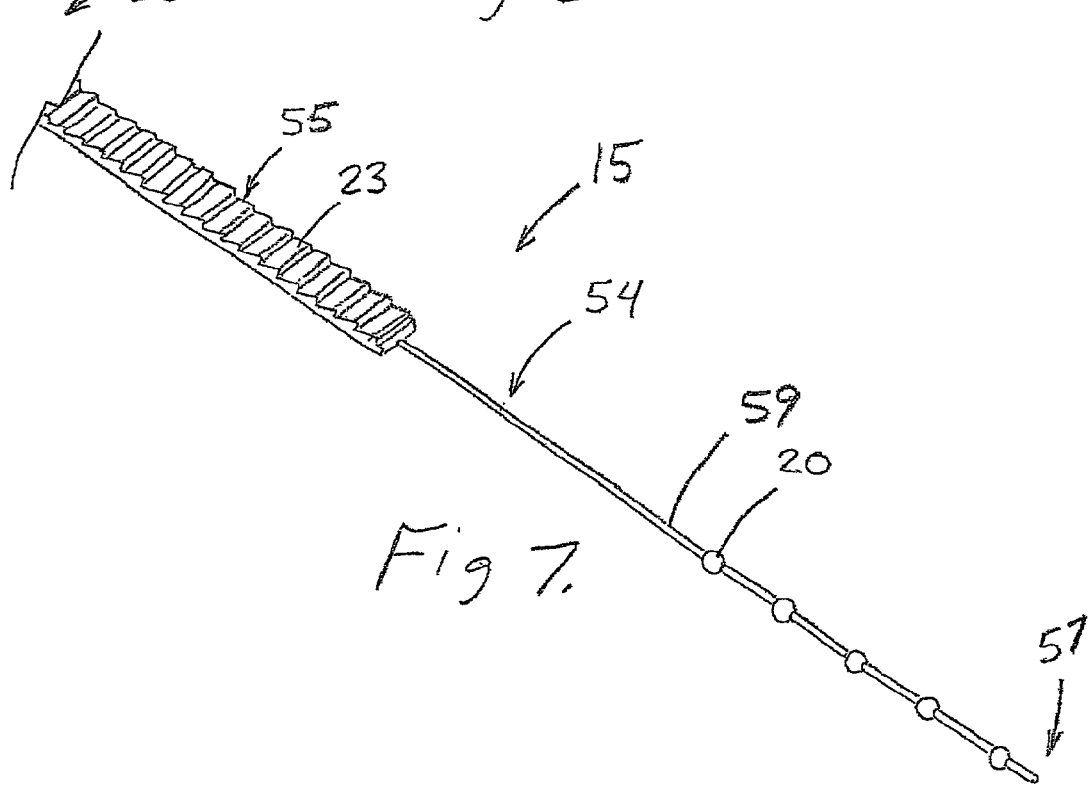
FIG. 7 depicts a pictorial view of the band carrier element of FIG. 1.

A first illustrative embodiment of the multiple ligating band delivery apparatus 10 of the present invention is depicted in FIG. 1, comprising a delivery member 11 with a passageway 22 extending therethrough; a pair of ligating band carrier elements 15, each having a first portion 54 that holds a plurality of preloaded ligating bands 17 over the delivery member 1. In its pre-deployment state, the remainder of the band carrier element 15 (including the second portion 55) at least partially resides within passageway 22. The band carrier elements 15 of the present invention can vary in number and configuration, but generally the first portion 54 includes a plurality of spaced retainers 20 that maintain the ligating bands 17 in a fixed position relative to the band carrier element 15 until the most distal ligating band 18 is deployed. The band carrier elements 15 operate much like a conveyer belt to pull the retainers 20 toward the proximal end, then over the distal edge 21 of the delivery member 11 and finally, into the passageway 22 once the ligating band is released. Therefore, the band carrier elements 15 should be made from materials or a design that allows them to flex or articulate over the distal edge 21 at which point they essentially fold over and fully reverse direction as the band carrier elements 15 are being engaged and pulled inward. In the illustrative embodiment, which is also depicted in FIG. 7, the first end 57 of the band carrier element 15 is initially external to the passageway 22, while the second end 58 is located within the passageway 22. The first portion 54 of the band carrier elements 15 comprises a strand-like portion 59 of material having a relatively high tensile strength, such as VECTRAN® fiber (Celanese Chemicals, Dallas, Tex.) or another suitable material such as nylon, metal wire, etc. Located at regular intervals along the first portion 54 of the band carrier elements 15 are retainers 20, which in the illustrative embodiment, comprise polycarbonate beads placed over, and secured to the strand-like portion 59. Alternatively, the retainers 20 and the strand-like portion 59/band carrier element 15 can be fabricated together as a single piece of material. In another alternative embodiment, the band carrier element 15 can be a continuous, belt-like element (not illustrated) that feeds into the passageway 22 at the distal edge 21 and then back out of the passageway 22 via an aperture through the delivery member 11 located proximally therealong.

As best depicted in FIG. 7, the illustrative band carrier element 15, having an overall length of approximately 441 (10–11 cm), comprises the first portion 54 that includes the strand-like portion 59 and four bead-like retainers 20 placed at about 0.25" (5–6 mm) intervals with respect to each other, and a second, band-like portion 55 that includes a plurality of coupling elements 23, such as a series of closely adjacent teeth. The second portion 55, which includes approximately 35–40 teeth 23 (coupling elements) in the illustrative embodiment, is coupled with the second portion by bonding or insertion of the strand-like portion 59 into the second portion 55 The teeth 23 are configured to engage with a locking element 26 and a actuating coupler 24, which are depicted in FIG. 1 and will be more fully disclosed below. The shape of the teeth 23 in the illustrative example are about 0.03" (0.8 mm) high, 0.07" (1.8 mm) long, and have an orientation angle of about 30° toward the proximal end 56 of the device (with 0° being completely flat relative to the longitudinal axis of second portion 55). This configuration restricts the movement of the teeth relative to the oppositely oriented locking element 26 or actuating coupler 24 to a single direction of movement, i.e., movement of either the band carrier element 15 and coupling elements 23 or the component that includes the locking element 26 or actuating coupler 24, must be in the same direction as the orientation angle of its opposing member. However, when the opposite occurs, such as when the component bearing the actuating coupler 24 is retracted in a direction opposite to the angle of the coupling elements 23 (i.e., when moving proximally), the actuating coupler 24 engages a proximate tooth 23 and does not permit the two elements to move further in opposite directions. When the actuating coupler 24 is urged in a proximal direction, it pulls the second portion of 55 of the band carrier elements 15 along with it, further into the passageway 22. This in turn, forces the first portion 54 to bend over the distal edge 21 and be drawn into the passageway 22. Movement of the band carrier elements results in the retainers 20 and loaded ligating bands 17, which are also depicted in FIG. 3, being advanced toward the distal edge 21. When the first retainer 20 approaches the distal edge 21 and begins the process of being drawn into the passageway 22, the first ligating band 18, which has been stretched over the delivery member 11 and band carrier elements 15 during the loading process, slides off the delivery member 11 and band carrier elements 15. A standard dilating tool is used for loading. As the ligating band 18 slides over the distal edge 21, it elastically returns to its original unstretched state, or at least attempts to do so, over the mass of tissue, such as hemorrhoidal tissue, that has been drawn by suction into a distal receiving chamber 31 which comprises the distal portion of the passageway 22. Continued advancement of the band carrier element results in the next retainer 20 be moved into position to release the second ligating band 19. Ideally, this is accomplished automatically with a single manual deployment of the actuating mechanism 32, embodiments of which are described below. The standard hemorrhoid ligating band used with the present invention is a black natural rubber band manufactured by Ford Dixon Co. of Ft. Worth, Tex. which has an O.D. of 0.190" and an I.D. of 0.06".

The retainers 20 can be given any shape or configuration that functions to urge the ligating bands 17 toward the distal edge 21 when the band carrier elements 15 are advanced. Other examples of band carrier elements 15 are shown in FIGS. 4 and 5. In FIG. 4, the entire band carrier element 15 comprises a flat, band-like structure that glides over the surface of the delivery member 11. The retainers 20 each comprise a raised protuberance or enlarged member that holds the ligating band 18 in position and urges it toward the distal edge 21 when the band carrier element 15 is advanced. FIG. 5 depicts an embodiment similar to that in FIG. 4, with the retainer comprising a hooked process 52 for more positive engagement with the ligating band 18. Alternative retainer 20 embodiments could include various forms of tethers or even adhesives than would permit the ligating bands 17 to be urged distally, but still allow the ligating bands 17 to release from the delivery member 11 as they reach the distal edge 21 of the device. Other modifications to the above embodiments include placing a second retainer in front of the ligating band for extra support, and forming a channel or recess in the delivery member in which the band carrier element may reside and slide therewithin.

Again referring to FIG. 1, the illustrative embodiment an actuating assembly 60 comprising an internal engagement assembly 12 that engages the second portion 55 of the band carrier elements 15, which pulls the band carrier elements 15 into the passageway 22, thereby advancing the ligating bands 17 over the delivery member 11. The components of the illustrative internal engagement assembly 12, like the delivery member 11, are typically made out of a polymer, such as polycarbonate. In the embodiment of FIG. 1, the internal engagement assembly 12 comprises an engagement member 13 that is slidably disposed within the passageway 22 of the delivery member 11 and functions to engage the second portions 55 of the band carrier elements 15 to progressively pull the first portions 54 thereof, over the distal edge 21 of the delivery member 11 and into the passageway 22. Engagement between the band carrier elements 15 and the engagement member 13 is accomplished by engagement with the series of coupling elements 23, such as tooth-like projections, that are distributed along the second portion 55 of the band carrier elements 15, and configured to intermesh with a corresponding tooth-like actuating coupler 24 located within opposing longitudinal channels 25 are formed in the engagement member 13. These channels 25, which are also depicted in FIG. 2, are sized to accommodate the band carrier elements 15 and allow them to slide freely therein. The actuating coupler 24 and plurality of coupling elements 23 are configured and arranged to permit the actuating coupler 24 to freely advance over the coupling elements 23 of the stationary band carrier elements 15, but positively interlock with one of the coupling elements 23 once as the engagement member 13 moves in a proximal direction relative to the band carrier elements 15.

A second, separate component of the internal engagement assembly 12 of the illustrative embodiment is an insert member 14 which fixed within the passageway 22 at a location distal to the engagement member 13. The stationary insert member 14 includes the aforementioned locking element 26 which is also configured to engage the coupling elements 23 of band carrier elements 15 and prevent the band carrier elements from moving in the direction opposite to that traveled during normal deployment. This inadvertent reverse movement of the band carrier elements 15 could result if sufficient friction occurs when the engagement member 13 is sliding over the coupling elements 23 during its advancement, or by contact of the apparatus 10 with a bodily surface. To prevent this from occurring, a pair of locking elements 26, similar in shape to the actuating coupler 24, are located within opposing longitudinal channels 27 of the insert member 14. The interface between the locking element 26 and the band carrier element 15 is very similar to that of the engagement member 13, a cross sectional view of which is depicted in FIG. 2. Like the actuating coupler 24, the locking element 26 is designed to allow relative movement with the band carrier elements 15 in one direction. However, unlike the engagement member 13, the insert member 14 is fixed within the passageway 22 of the delivery member 11, such as by being press-fitted or bonded therein. Therefore, the locking element 26 only permits the band carrier elements 15 to move proximally relative to the insert member 14 and delivery member 11.

Although the insert member 14 is not necessarily a critical component of the general embodiment depicted in FIG. 1, it advantageously facilitates engagement between the engagement member 13 and band carrier elements 15 to permit more predictable and reliable operation. As an alternative to the insert member 14, the delivery member 11 itself could be configured to include inner channels and one or more locking elements 26 to engage the band carrier elements 15, or one of a multitude of other possible arrangements to accomplish the same, or a similar function. The means for engagement between the band carrier elements 15 and the engagement member 13 is certainly not limited to that shown in the illustrative embodiment. An ordinary person skilled in the mechanical arts would readily recognize that numerous possibilities and variations exists that would solve the problem of drawing the illustrative band carrier elements 15 into the passageway 22 to sequentially deploy the ligating bands. The engagement member 13 can intermesh with, grab, hook, or otherwise engage coupling elements 23 located on the band carrier elements 15 to pull the first portion 54 into the passageway 22 and advance the ligating bands 17. These coupling elements 23 may consist of any type of protuberance, ridge, aperture, etc. that would facilitate positive engagement with the actuating coupler 24 It would also be within the scope of the invention to eliminate the coupling elements 23 from the band carrier element 15 and to have the engagement member 13 to directly engage the band carrier elements 15. Another possibility is that the engagement member 13 does not directly engage the band carrier elements 15. In one example, each band carrier element could comprise a single strand or wire that is taken up on separate gear-like spools or wheels that include a plurality of teeth. When the advancement/engagement mechanism is urged proximally, it engages the teeth and turns the spools. The strands are taken up by the spools, thereby drawing the band carrier elements into the passageway and causing deployment of the ligating bands. The engagement member would be configured to freely slide over the teeth of the spools during retraction, thereby not permitting them to reverse the spools and unwind the strand.

The illustrative embodiment of FIG. 1 is adapted for single-handed operation. To accomplish this, the illustrative engagement member 13 is connected to a proximal actuating mechanism 32 comprising a proximal actuator 34, a biasing member 35, such as a compression spring, and grip portion 33. The illustrative ligating band delivery apparatus 10, which is sized for treating hemorrhoids, measures approximately 8 inches in length, with the delivery member 11 comprising about first 6.5 inches of that length and the remainder primarily comprising the proximal actuator 34. The OD of the delivery member is about 0.5" prior to the distal tapered portion (about 1.8" in length), where it tapers to about 0.36" at the distal end 21. These dimensions are merely illustrative and thus, subject to variation according to design preference. In the illustrative embodiment, the actuating member 13 is affixed within the internal member receiving chamber 36 of the proximal actuator 34, which is open distally, via a pressure-fit engagement or a well-known method of bonding. The engagement member 13 is prevented from exiting the distal end 46 of the delivery member 11 by a stopper 16 which is inserted thereinto. The stopper 16 provides the surface against which the distal end of the spring 35 is urged, with the proximal end of the spring being inserted into a annular recessed channel 51 formed in the proximal actuator 34. The actuating mechanism 32 allows the operator to apply manual force in a distal direction that transferred from the proximal actuator, typically via the palm or thumb of the operator, to the engagement member 13, which is connected therewith. This in turn, urges the engagement member 13 forward until the distal end 45 of the proximal actuator 34 contacts the proximal surface 46 of the grip portion 33, this space being slightly shorter is distance (0.237") than the throw space 30 (0.30") which separates the engagement member 13 from the fixed insert member 14 prior to deployment. Alternatively, it also would be possible to have the forward advancement of the engagement member 13 limited by contact with the insert member 14 by making the throw space 30 the shorter distance of the two. The actuating coupler 24 located on the engagement member 13 advance over a particular number of teeth 23 (coupling elements) of the band carrier elements 15 (about 5 in the illustrative embodiment). When the operator ceases to apply the force required to maintain the forward position of the engagement member 13, the compressed spring 35 urges the engagement member 13 in a proximal direction, thereby allowing the actuating coupler 24 to engage the teeth 23 of the band carrier elements 15 and pulling the second portion 55 thereof in a proximal direction over a predetermined distance that results in a retainer 20 being moved to the correct position for deployment of a ligating band 18. While the exemplary actuating mechanism 32 provides a simple to use, low-cost solution of the problem of providing a operative engagement between the band carrier elements 15 and the engagement member 13, a skilled person in the mechanical arts would certainly appreciate that there are a number of methods of accomplishing the same task. For example, a similar design could be used, except that the compression spring 35 would be replaced by a tension spring, whereby the actuating mechanism 32 or engagement member 13 is configured to lock in the fully advanced position, then released to deploy the individual ligating bands 17.

Other types of handles or actuating mechanisms could be used that would still permit single-hand operation, including pistol or trigger-type handle assemblies, or standard three-ring handles, with or without a biasing member 35 as part of the mechanism. Additionally, the actuating mechanism 32 may include a electrical, pneumatic, or other powered mechanism operable by depressing a button or switch. It is not necessary to the invention that the internal engagement assembly 12 be advanced to engage the band carrier elements 15, only that the band carrier elements 15 be pulled into the passageway 22 to urge the retainers 20 and ligating bands 17 toward the distal edge 21 of the apparatus 10. Furthermore, it is not essential, in this particular embodiment type of the present invention, that the internal engagement assembly 12 be strictly located internal to the delivery member 11, only that the particular system used results in the band carrier elements 15 being drawn further into the passageway 22 of the delivery member 11 during manipulation by the operator. In fact, the band carrier elements 15, the engagement member 13, and the actuating mechanism 32 are not required to be separate components, but rather certain elements may be absent or combined into a single structure having more than one function. For example, in its simplest form, the band carrier element could merely comprise a strand or cable in which the second end thereof is extended into and through the passageway where it exits the proximal end and can be grasped to urge the first portion of the band carrier elements into the passageway to deploy the ligating bands.

FIG. 6 depicts a ligator band apparatus 10 of the present invention being used to apply a ligating band 18 over portion of hemorrhoidal tissue 53. In each of the illustrative embodiments, the hemorrhoidal tissue 53 is drawn into a receiving chamber 31 which comprises the distal portion of the passageway 22 of the delivery member 11. In the main illustrative embodiment, the receiving chamber has an ID of about 0.355" and extends into the passageway 22 for a distance of approximately 0.45", ending at the distal end 44 of the insert member 14. After the tissue 53 has been drawn into the receiving chamber 31, the ligating bands 17 are then deployed over the hemorrhoidal tissue 53, cutting off blood flow, which leads to tissue necrosis. Eventually, the dead tissue falls away, along with the band, leaving healthy tissue that finishes healing beneath the original constriction. To draw the hemorrhoid or other type of tissue into the receiving chamber 31, a suction device is used, such as the standard hospital unit or system used for such purposes. Alternatively, the apparatus 10 may include, or be connectable to a syringe or other device capable of creating a vacuum to draw the tissue into the receiving chamber 31.

Returning to FIG. 1, the illustrative apparatus 10 includes a suction means attachment port 37 located on the proximal actuator 34 that connects to an external suction unit 50. The suction means attachment port 37 communicates with the distal receiving chamber 31 via series of passageways. In the illustrative embodiment, the suction means attachment port 37 includes a main suction passageway 39 that communicates with the engagement member passageway 28, which in turn, communicates with the insert member passageway 29, via the throw space 30. The insert member passageway 29 directly communicates with the distal receiving chamber 31 which is open distally. To ensure that adequate suction can be created at the distal receiving chamber 31, the inner space 49 between the engagement member 13 and the delivery member 11 is sealed with a gasket 47 that in the illustrative embodiment, resides within a recess 48 formed in the engagement member 13. The gasket 47 assists in maintaining a constant positional relationship between the two members 11, 13, while still allowing the engagement member 13 to slide freely within the passageway 22. To draw the tissue into the distal receiving chamber 31, the operator places his or her thumb or palm over the proximal opening (suction actuating interface 40) located at the proximal end 56 of the apparatus 10 to create sufficient suction about the distal end 21 of the device. The suction actuating interface 40 functionally communicates with the main suction passageway 39 via the actuating passageway 38, which is in line with the passageway 22 of the delivery member 11, the main passageway making a 90° bend at the junction with the actuating passageway 38. Once banding has occurred, the operator uncovers the proximal opening 40, breaking the suction such that the tissue 53 is no longer being drawn into the distal receiving chamber 31. The depicted method of controlling suction within the distal receiving chamber 31 is merely illustrative. Other systems and configurations are available that would essentially accomplish the same result.

FIGS. 8–11 depict another embodiment of the present invention of the ligating band delivery apparatus 10 in which the proximal portion 61 includes a grip portion 33 that extends at an angle from the delivery member 11, much like the handle of a pistol, such that it generally fits within the palm of the operator's hand, while the delivery member 11 extends distally therefrom, much like the barrel of a pistol. The illustrative embodiment is configured so that the operator can operate the actuating mechanism 32, which comprises a knurled wheel 70, with the thumb of one hand, while the suction actuation interface 40, which is conveniently located about the distal face 88 (the generally forward directed surface or edge) of the grip portion 33, is selectively opened and closed using a finger of that same hand, such as the index or middle finger. Thus, the other hand is free to manipulate an anoscope while treating hemorrhoids within a patient. Although the illustrated distal face 88 is generally flat and distinct from adjacent surfaces of the grip portion 33, it may also comprise a different shape or configuration, such as a rounded distal face 88 or surface.

Figure 8:
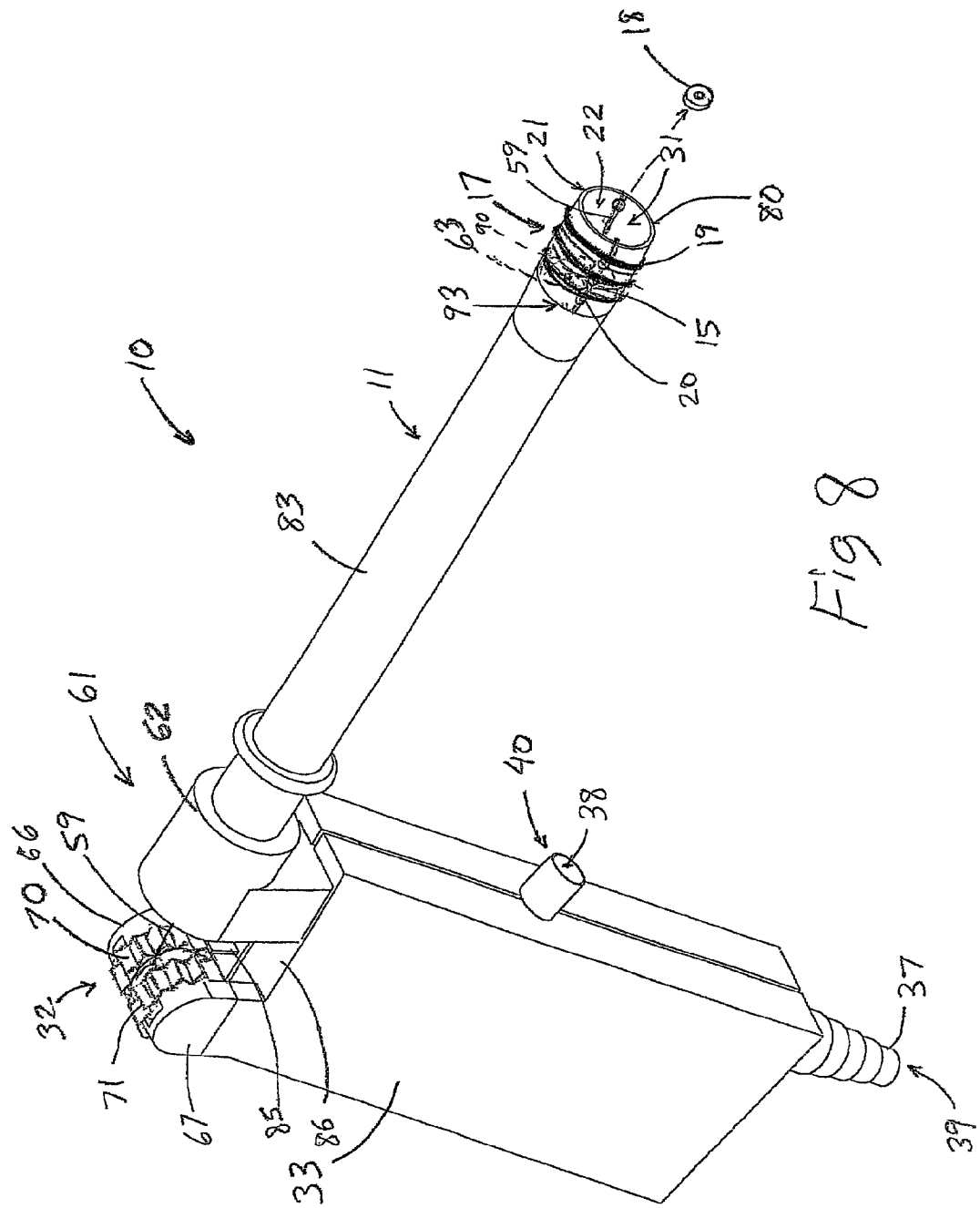
FIG. 8 depicts a pictorial view of another ligating band apparatus of the present invention having a grip portion that is pistol-shaped.
Figure 9:
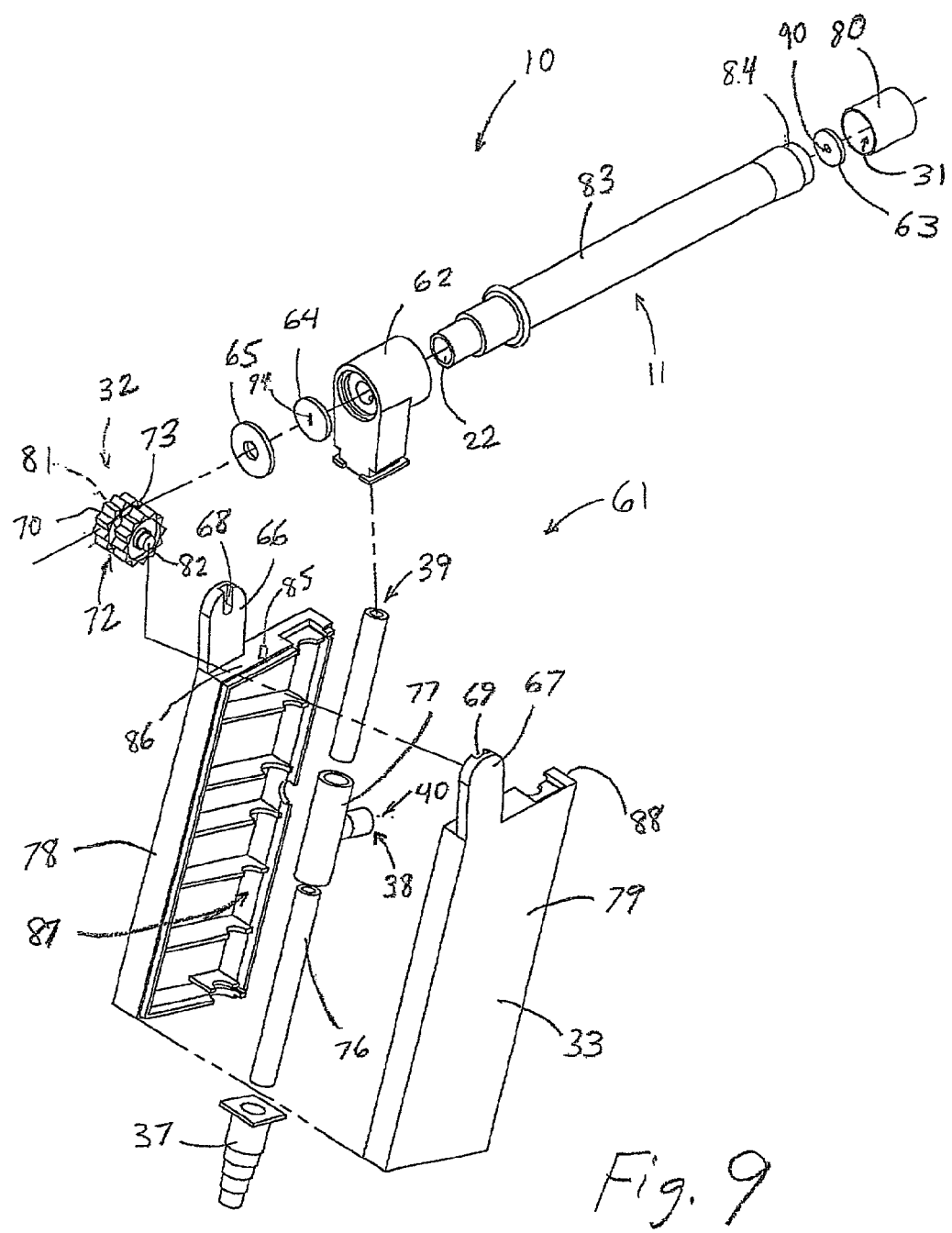
FIG. 9 depicts an exploded view of the embodiment of FIG. 8.

Referring now to both FIG. 8, which depicts a pictorial view of the present invention, and FIG. 9, which shows an exploded view of same, the majority of the components, including the delivery member 11 and external housing of the proximal portion 61, are made from a rigid polymer, such as polycarbonate. The illustrative delivery member 11, which includes the passageway 22 extending therethrough, comprises a proximal barrel portion 83, which inserts into a proximal receiving element 62 mounted onto the upper surface 86 of the grip portion 33 of the proximal portion 61. The delivery member 11 further includes a distal tip portion 80, attached over the distal lip 84 of the barrel portion 83, the distal tip portion 80 preferably comprising a clear polymer, such as polyurethane, to allow visibility of the tissue within the tissue receiving chamber 31. The tissue receiving chamber 31 is the space comprising the passageway 22 within the distal tip portion 80 that proximally terminates at a distal orifice plate 63 that rests against an internal lip within the distal lip 84 of the barrel portion 83. The orifice 90 of the distal orifice plate 63 measures approximately 2.5 mm and communicates with the passageway 22 extending through the barrel, which comprises a portion of the main suction passageway 39 that connects with the external suction apparatus 50 (not shown). The tissue receiving chamber 31, which in the present embodiment is configured to accept a amount of hemorrhoidal tissue sufficient for banding, measures about 1 cm in length and has an I.D. of approximately 0.9 cm at the distal orifice plate 63, tapering only slightly toward the distal edge 21. The length of the delivery member, including the distal tip portion 80, from the distal end of the proximal receiving element 62 to the distal edge 21 is approximately 128 mm in the illustrative embodiment, with a range of 100 to 150 mm being most acceptable, clinically.

The present invention is adapted to sequentially deliver a series of ligating bands 17 with one insertion of the apparatus 10 into the patient. The ligating bands 17 are loaded over the distal tip portion 80 of the delivery member by dilating them using a standard loading device. Located between the outer surface of the delivery member 11 and the individual ligating bands 17 is the ligating band carrier element 15, which in the illustrative embodiment of FIG. 8, comprises a strands 59 comprising a thread or suture made of a braided or monofilament polymeric material, a natural fiber, metal wire, or other suitable material. One example of material having the necessary tensile strength is VECTRAN® fiber (Celanese Chemicals, Dallas, Tex.). FIG. 11 depicts an embodiment of the band carrier element 15 adapted for use with the embodiment of FIG. 8 in which there are two strand portions 59 that are secured against the distal tip portion 80 by the ligating bands (as shown in FIG. 8A), allowing the ends 93 of the strands 59 to be otherwise unattached to the apparatus 10. From there, the strands 59 extend distally before being inverted into the tissue receiving chamber 31, orifice 90 and passageway of the delivery member 11, where they are united into a single yoke portion 91, as depicted in FIG. 11. The illustrative the band carrier element 15 either can be considered to be a single structure with either two strands 59 united by the yoke portion 91, or as two band carrier elements 15 that are joined proximally. Additionally, an embodiment having separate strands 59 that are uncoupled to one another, but functionally joined at the actuating mechanism 32 (knurled wheel 70), is considered to be a either single band carrier element 15 or two separate ones for purposes of the claims.

At the midpoint of the strand portions 59 is a central knot 94, from which the yoke portion 91 extends proximally to engage the proximal actuating mechanism 32, in particular, a knurled wheel 70 or similar type of mechanism that can apply continual tension to the band carrier element 15 to urge it into the passageway 22, thereby deploying the ligating bands loaded thereover. In the illustrative knurled wheel 70, shown in detail in FIGS. 10–12, there is a central recessed portion 72 for accommodating the band carrier element 15 as it is spooled over the knurled wheel 70 during band deployment. Within the central recessed portion 72 is a generally ovoid recess 75 for receiving a proximal knot 92 (FIG. 12) of the yoke portion 91 to attach the band carrier element 15 to the knurled wheel 70. The yoke portion 91 is sized to fit within a T-shaped channel 73 within the central recessed portion 72; however, the proximal knot 92 abuts against the opening to the channel 73, thus providing a releasable, but secure engagement as the knurled wheel 70 is rotated to spool the band carrier element 15 during deployment. In the illustrative embodiment, additional strands are braided into the yoke portion 91, providing increased thickness that aids with engagement, as well as increasing its strength. One skilled in the mechanical arts would recognize that FIGS. 10–12 depict just one of many possible solutions for providing a coupling engagement between the band carrier element 15 and the actuating mechanism 32.

To urge the ligating bands 17 distally in the direction of the distal edge 21 for deployment around target tissue, the band carrier element 15 includes a plurality of spaced retainers 20, which in the illustrative embodiment (FIG. 11) comprise beads of silicone located at selected intervals along the string. In the illustrative example, retainers 20 are located at about 3 mm from the ends 93 of the strands 59 and at about 25 mm intervals therefrom for a total of four retainers 20 on each strand 59. The silicone beads comprising the retainers 20 are approximately 1 mm in diameter. The ligating bands 17 are loaded over the tip to rest against a corresponding pair of retainers 20 on the opposing strands 59. When the ligating band carrier elements 15 are drawn into the passageway 22, the abutting retainers 20 help urge the ligating bands 17 distally, as they being carried along with the band carrier element 15, until they are deployed over the distal edge 21.

FIG. 8A depicts an enlarged view of an exemplary distal tip portion 80, illustrating how the configuration of the strands 59 of the band carrier element 15 prior to deployment of four ligating bands 17. In the illustrative example, the strands 59, as they extend out of the passageway 22 and fold over the distal edge 21 of the delivery member 11, pass under the first ligating band 18 at approximately the three o'clock and nine o'clock positions of the band. At that point, the first retainer 96 is positioned directly behind the first ligating band 18. From the first retainer 96 on first side 110 of the delivery member 11, the strand is oriented downward to create a partial wrap 108 across the second half 111 of the distal tip portion 80 and around the circumference thereof until reaching the vicinity of the first retainer 96, where it makes a approximately 90° bend 109 and passes under the second ligating band 19, at which point, the second retainer 97 is located. The strand 59 then is wrapped up over the top of the distal tip portion 80 and around the circumference thereof to a point near the second retainer 97, where it passes until the next band to where the third retainer 98 is located. At that point, the wrapping sequence used for the first two bands 18, 19 is repeated for the remaining two bands.

Referring now to FIGS. 8 and 12, once the band carrier element 15 has been secured to both the delivery member 11, distally by the plurality of ligating bands 17, and proximally by the knurled wheel 70, the proximal actuating mechanism 32 can be conveniently used to deploy the ligating bands 17 by simple manual operation, such as the operator placing a thumb on the knurled wheel 70 and causing it to rotate downward to place increased tension on the band carrier element 15 until the most forward positioned ligating band 18 is deployed. The operation is repeated for each band to be deployed. A rachet mechanism 85, such as a tooth or structure of similar function, is located on the upper surface 86 of the grip portion 33 that engages the teeth of the knurled wheel 70 as it is manually rotated, thereby preventing the wheel from rotating in the opposite direction, which would reduce tension on the band carrier element 15. As shown in FIG. 10, the first axial spindle 81 is smaller than the second axial spindle 82, as are the corresponding mounting slots 68,69 formed in the two mounting brackets 66,67, thereby facilitating correct placement of the knurled wheel 70 during assemble such that the ovoid recess 75 and channel 73 are properly oriented to engage the band carrier element 15.

The illustrative embodiment is configured such that when the operator places the grip portion 33 in the palm of the hand, the knurled wheel 70 of the proximal actuating mechanism 32 is conveniently located such that it can operated by the thumb of that hand, while the suction actuating interface 40 is located on the distal face 88 of the grip portion 33 such that the lateral pathway 38 leading thereto, can be selectively opened or closed by a finger on the grip portion 33, typically the index or middle finger of the same hand. The illustrative suction actuating interface 40 comprises a short length of polymer tubing that extends from a standard T-fitting 77, shown in the exploded view of FIG. 9., which partially resides within the internal support channel 87 defined by the two halves 78,79 of the grip portion 33. From the T-fitting 77, two separate sections of tubing 76, coupled thereto, extend in opposite directions to connect with the proximal receiving element 62 at the top, and the suction means attachment port 37 at the bottom of the grip portion 33, thereby forming the main suction pathway 39 of the proximal portion 61 of the apparatus 10. The passageway 22 of the delivery member 11 forms the remainder of the main suction pathway 39 which creates enables suction to be created within the tissue receiving chamber 31 when the suction actuating interface 40 is sealed and the apparatus 10 is connected to a suction device. Referring also to FIG. 12, the proximal receiving element 62 includes a seal 64 at the back, comprising a low-durometer polymer or material with similar properties, that includes a slot 112 through which the yoke portion 91 or strands 59 of the band carrier element 15 passes while not causing a sufficient break in the suction that would compromise effective aspiration of tissue into the tissue receiving chamber 31. A back plate 65, which is pressure-fitted or bonded with the proximal receiving element 62 helps secures the seal 64 therein.

Figure 14:
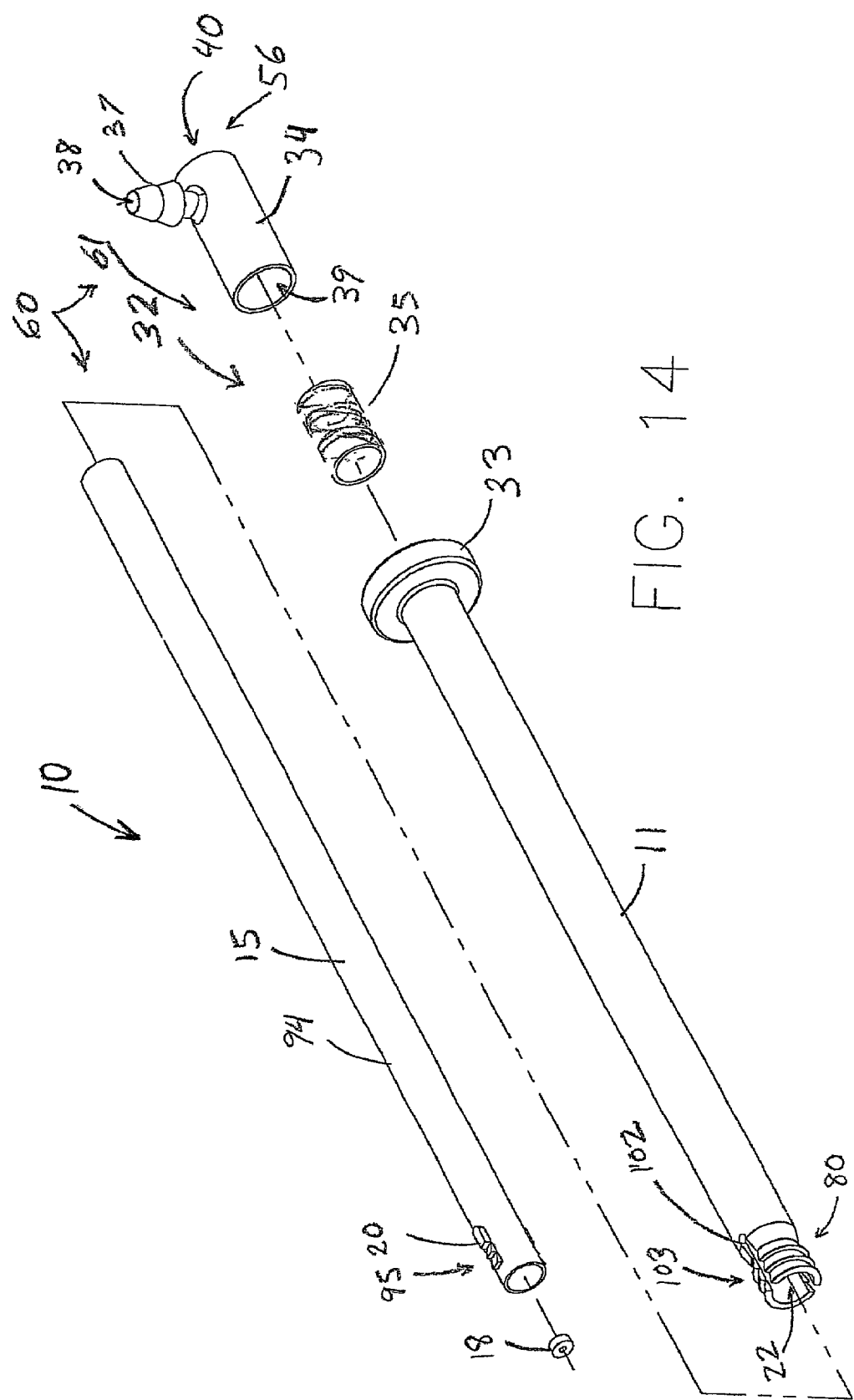
FIG. 14 depicts an exploded view of the embodiment of FIG. 13.
Figure 15:
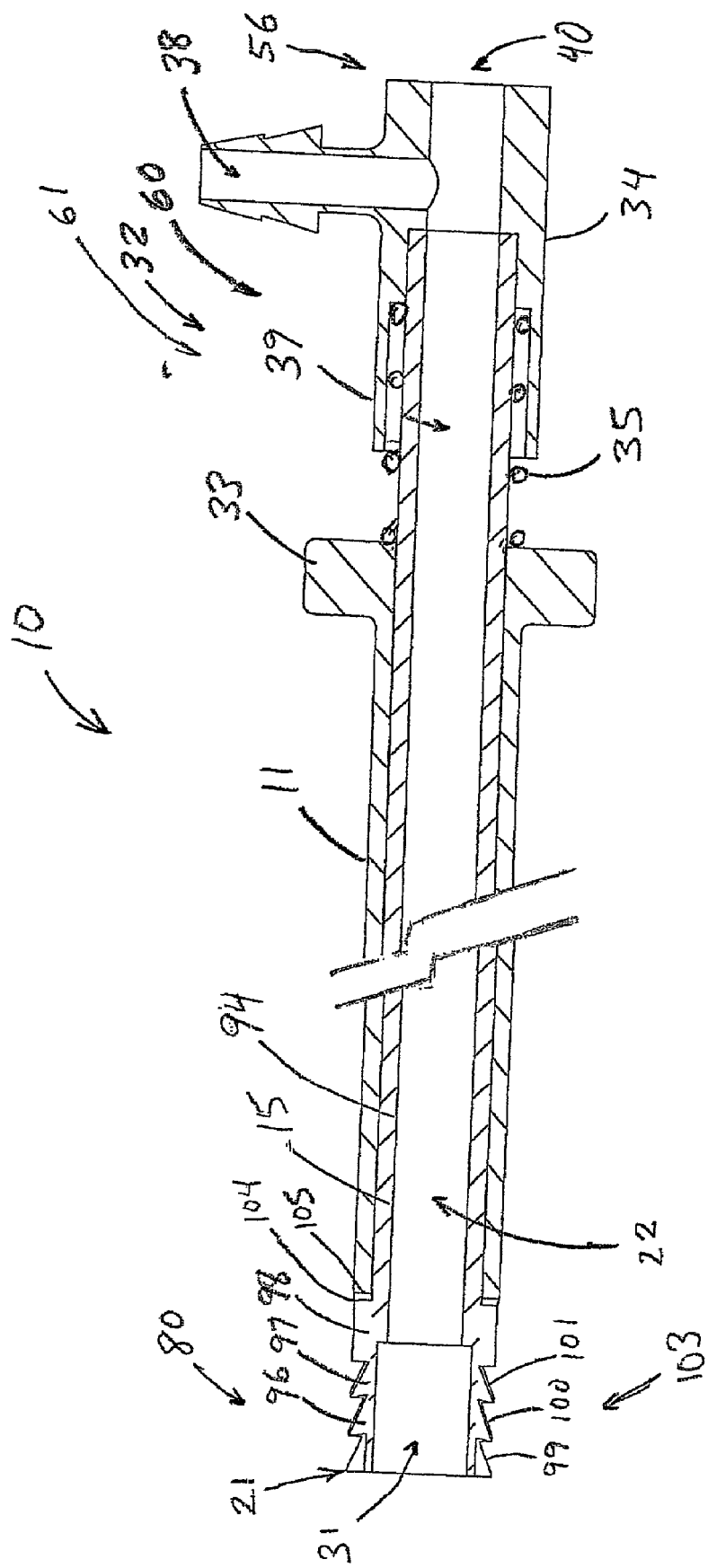
FIG. 15 depicts a sectioned side view of the embodiment of FIG. 13.

FIGS. 13–17 depict another embodiment of the present invention in which the band carrier element 15 comprises a coaxial inner tubular member 94 with the retainers 20 comprising two series of tooth-like projections 95, each located at approximately 180° with respect to one another. Referring to FIGS. 13–16, the distal tip portion 80 includes a series of steps 103, each step 99,100,101 providing a loading position for an individual ligating band 18, which in the illustrative example in FIG. 16, is loaded onto step 100. It should be noted that the steps 103 may decrease in outer diameter toward the distal end 21 of the distal tip portion 80, or be substantially of the same diameter and have a ramped configuration, as in the illustrative example. As shown in FIGS. 13–15,17, there are three projections 95 which correspond to the three steps 103 of the delivery member 11 when the inner tubular member 94 is disposed within delivery member 11. A pair of opposing longitudinal channels 102 (FIGS. 13–14,16) received the projections 95 and allow them to slide distally within the channels 102 as the inner tubular member 94 is advanced relative to the outer delivery member 11. The projections 95 are configured to abut the proximal edge of the ligating band 18 and urge that particular band toward the distal edge 21 of the outer delivery member 11. Referring now to FIGS. 13–15, the inner tubular member 94 and projections 95 are advanced relative to the delivery member 11 and loaded ligating band 18 by means of the proximal actuating mechanism 32, which together with the inner tubular member 94, comprises the actuating assembly 60 for advancing a ligating band 18. The illustrative proximal actuating mechanism 32 is similar in structure and function to the embodiment depicted in FIG. 1, which also includes a grip portion 33, proximal actuator 34, and biasing member 35 that is attached to the proximal actuator 34 with a receiving chamber 36 (FIG. 15). The primary difference with the embodiment of FIG. 1 is that rather than attaching to an internal engagement assembly 12 that in turn, engages the band carrier element 15, the biasing member 35 directly actuates the band carrier element 15, which in the embodiment of FIGS. 13–17, is the inner tubular member 94. The manner by which the suction is supplied and controlled (e.g., locating the suction actuating interface 40 at the proximal end 56 of the device 10) is also very similar to the embodiment of FIG. 1.

Referring particularly to FIGS. 16–17, the function of the projections 95 is to urge the ligating band 18, which is typically at its resting position 106 at the proximal end of the step 100, forward over the distal edge 107 of the step 100, which is angled outward from the resting position 106 to help maintain the ligating band 18 on the step 100 until deployment. This angled tooth-like shape that provides a ramp for deploying the ligating band and maintaining a stable pre-deployment position. In contrast, the proximal projection 98, where there is no band to be deployed thereover, conveniently includes a raised proximal edge 104 for abutting the proximal end 105 of the longitudinal channel 102 and limiting relative movement in that direction. In the case of the ligating band 18 shown in FIG. 16 and located on step 100, the second projection 97 (FIG. 17) comprises the retainer 20 for the ligating band 18 at that position (typically the second of three bands to be deployed). The band carrier element 15 is advanced relative to the delivery member 11 when the operator urges the grip portion 33 and proximal actuator 34 toward one another by compressing the biasing member 35. This causes the projection 97 to slide the ligating band 18 from step 100 to step 99. The third projection 98 will urge the band located at step 101 forward to replace the band 18 originally located at step 100. If the original band located at step 99 still has not yet been deployed over the distal edge 21 of the delivery member 11, it will occur at that time as the first tooth 96 urges it forward simultaneous with the second tooth 97 urging the second ligating band 18 onto step 99 to take its place. If a third deployment is required, the final band is deployed from step 99 after first being urged from step 101 and 100, respectively, during the first two band deployments. Of course, the present embodiment could be adapted for deployment of four or more ligating bands by adding the appropriate number of steps 103 and projections 95.

Although the illustrative band ligating apparatus of the present invention is depicted as being adapted for delivering multiple bands and single-hand operation as a stand-alone apparatus, the disclosed delivery mechanisms could easily be adapted for single-band application and/or use with an endoscope. In addition, one skilled in the medical or mechanical arts would recognize that the three main exemplary delivery mechanisms could be adapted to be used with a different actuating mechanism than shown. For example, the band carrier elements of FIG. 1 could easily be adapted for use with the pistol-style proximal portion 61 and proximal actuating mechanism 32 of FIG. 8 or other actuating mechanisms not specifically disclosed. Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The inventor contemplates embodiments both comprising and consisting of the described elements. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, $27^{th}$ edition.

What is claimed is:

1. A ligating band delivery apparatus for delivering a plurality of ligating bands within a patient, comprising:
    a proximal portion for hand held operation, the proximal portion generally fitting within the palm of the operator's hand;
    a delivery member for receiving a plurality of ligating bands which are loadable thereonto, the delivery member comprising a distal end and a proximal end, a tissue receiving chamber located about the distal end, and a passageway extending proximally from the tissue receiving chamber;
    at least one ligating band carrier element configured for sequentially urging the plurality of ligating bands toward the distal end of the delivery member;
    an actuating assembly that includes a proximal actuating mechanism located about the proximal portion of the delivery apparatus and operatively connected to the at least one ligating band carrier element the proximal actuating mechanism comprising a spool;
    a main suction passageway comprising the delivery member passageway, the main suction passageway communicating with a suction means attachment port located about the proximal portion of the delivery apparatus;
    a suction actuating interface that communicates with the main suction passageway to control the presence or absence of suction at the tissue receiving chamber, the suction actuating interface configured such that an operator can simultaneously operate the suction actuating interface and actuating mechanism, while one hand remains free to perform other operations.

2. The delivery apparatus of claim 1, wherein the at least one ligating band carrier element comprises at least one strand configured for urging the plurality of ligating bands toward the distal end for deployment therefrom, the actuating mechanism configured for providing tension on the at least one band carrier element that urges the at least one strand into the passageway of the delivery member.

3. The delivery apparatus of claim 2, wherein the proximal portion includes a pistol type handle.

4. The delivery apparatus of claim 3, wherein the actuating mechanism includes a knurled wheel, the knurled wheel adapted to spool the strands thereonto when rotated in a particular direction by the operator, the knurled wheel configured to rotate in a single direction only.

5. The delivery apparatus of claim 1, wherein the proximal portion includes a pistol type handle having a distal surface, the actuating mechanism being configured to be actuated by the thumb of the operator to provide rearward tension on the at least one band carrier element, thereby allowing deployment of the plurality of ligating bands, the suction actuating interface located on the distal face of the pistol type handle such that it can be operated by a finger of the operator while the operator is grasping the pistol type handle.

6. The delivery apparatus of claim 5, wherein the at least one ligating band carrier element comprises a pair of strands that each include a plurality of retainers configured for receiving the plurality of bands and urging them toward the distal edge of the delivery apparatus.

7. The delivery apparatus of claim 1, wherein the at least one band carrier element comprises an inner tubular member disposed within the passageway of the delivery member, the inner tubular member including a plurality of retainers extending outward therefrom, each of the retainers configured for receiving one the plurality of bands and urging it toward the distal edge of the delivery apparatus.

8. The delivery apparatus of claim 7, wherein the delivery member includes an opposing pair of longitudinal channels for receiving the plurality of retainers and allowing them to slide longitudinally therein toward the distal end of the apparatus.

9. The apparatus of claim 1, wherein the at least one band carrier element includes a plurality thereof, each comprising a first portion and a second portion, wherein the second portion generally resides within the passageway of the delivery member, the second portion including a plurality of coupling elements that are engageable by an internal engagement assembly disposed within the apparatus and operatively connected to the actuating mechanism, the internal engagement mechanism adapted to simultaneously urge the plurality of band carrier elements further into the passageway, thereby allowing the plurality of ligating bands disposed over the first portion to be deployed.

10. The apparatus of claim 9, wherein the actuating assembly includes a plurality of actuating couplers located on the internal engagement assembly that are configured for engagement with the plurality of coupling members.

11. The apparatus of claim 10 wherein the internal engagement assembly further includes at least one locking element configured for engagement with selected ones of the plurality of coupling members, thereby preventing the band carrier element from moving in a direction opposite from that of deployment.

12. The apparatus of claim 1, wherein each of the at least one band carrier elements includes a first portion, generally disposed external to the passageway, that includes a plurality of retainers, and a second portion that is generally disposed within the passageway of the delivery member, the second portion being operatively connected to the proximal actuating mechanism.

13. The apparatus of claim 12, wherein the proximal actuating mechanism includes a grip portion located about the proximal end of the delivery member, a proximal actuator located proximal of the grip portion, and a biasing member attached to the proximal actuator, the proximal actuating mechanism is configured such that forward advancement thereof relative to the grip portion, causes at least selected ones of the plurality of retainers of the band carrier elements to be urged forward relative to the delivery member.

14. The apparatus of claim 13, wherein the proximal actuator and the biasing member are operatively connected to the least one band carrier element within the passageway of the delivery member such that advancement of the proximal actuator urges the entire length of at least one band carrier element forward relative to the delivery member.

15. The apparatus of claim 13, wherein the proximal actuator and biasing member are operatively connected to an internal engagement mechanism, the internal engagement mechanism configured such that it is engageable with the second portion of the least one band carrier element within the passageway of the delivery member, thereby urging the first portion of the at least one band carrier element at least partially into the passageway, thereby causing deployment of the plurality ligating bands.

16. A ligating band delivery apparatus adapted for delivering a plurality of ligating bands within a patient, comprising:

a proximal portion for hand held operation, the proximal portion generally fitting within the palm of the operator's hand;

a delivery member for receiving a plurality of ligating bands which are loadable thereonto, the delivery member comprising a proximal end, a distal tip portion having a distal edge, a tissue receiving chamber located about the distal tip portion, and a passageway extending proximally from the tissue receiving chamber;

at least one ligating band carrier element for sequentially urging the plurality of ligating bands toward the distal edge of the delivery member, the at least one ligating band carrier element comprising a strand like first portion that includes a plurality of retainers spaced therealong, and a second portion that is generally disposed within the passageway of the delivery member, the retainers adapted to carry and urge the ligating bands distally over the distal tip portion until deployment thereover;

an actuating assembly that includes a proximal actuating mechanism located about the proximal portion of the delivery apparatus that is operatively connected to the second portion of the at least one ligating band carrier element, such that operation of the proximal actuating mechanism urges the at least one band carrier element further into the passageway;

a main suction passageway comprising the delivery member passageway, the main suction passageway suction communicating with a suction means attachment port located about the proximal portion of the delivery apparatus;

a suction actuating interface that communicates with the main suction passageway to control the presence or absence of suction at the tissue receiving chamber, the suction actuating interface configured such that an operator can simultaneously operate the suction actuating interface and actuating mechanism, while one hand remains free to perform other operations.

17. The apparatus of claim 16, wherein the proximal actuating mechanism includes a grip portion located about the proximal end of the delivery member, a proximal actuator located proximal of the grip portion, and a biasing member attached to the proximal actuator, the proximal actuating mechanism is configured such that forward advancement thereof relative to the grip portion, causes the plurality of retainers of the band carrier elements to be urged forward toward the distal edge of the apparatus.

18. A ligating band delivery apparatus adapted for delivering a plurality of ligating bands within a patient, comprising:
- a proximal portion that includes a grip portion having a pistol type handle configuration that generally fits within the palm of the operator's hand;
- an elongate delivery member extending from the pistol type handle, the delivery member adapted for receiving a plurality of ligating bands which are loadable thereover, the delivery member having a distal edge, a tissue receiving chamber, and a passageway extending proximally from the tissue receiving chamber;
- a band carrier element for urging the plurality of ligating bands toward the distal edge of the delivery member, the ligating band carrier element comprising at least two strands that are retractable into the passageway;
- an actuating mechanism located about the proximal portion of the delivery apparatus comprising a knurled wheel that is operatively connected to the band carrier element, the knurled wheel configured to provide rearward tension on the band carrier element when the knurled wheel is rotated by the operator;
- a main suction passageway comprising the delivery member passageway, the main suction passageway suction communicating with a suction means attachment port located about the proximal portion of the delivery apparatus;
- a suction actuating interface that communicates with the main suction passageway to control the presence or absence of suction at the tissue receiving chamber, the suction actuating interface configured such that an operator can simultaneously operate the suction actuating interface and actuating mechanism, while one hand remains free to perform other operations.

* * * * *